US010368822B2

(12) United States Patent
Palma et al.

(10) Patent No.: US 10,368,822 B2
(45) Date of Patent: Aug. 6, 2019

(54) ITERATIVE X-RAY IMAGING OPTIMIZATION METHOD AND SYSTEM

(71) Applicant: General Electric Company, Schenectady, NY (US)

(72) Inventors: Giovanni John Jacques Palma, Buc (FR); Razvan Gabriel Iordache, Buc (FR); Serge Louis Wilfrid Muller, Buc (FR); Laurence Vancamberg, Buc (FR)

(73) Assignee: General Electric Company, Schenectady, NY (US)

( * ) Notice: Subject to any disclaimer, the term of this patent is extended or adjusted under 35 U.S.C. 154(b) by 227 days.

(21) Appl. No.: 14/840,675

(22) Filed: Aug. 31, 2015

(65) Prior Publication Data
US 2017/0055927 A1 Mar. 2, 2017

(51) Int. Cl.
*A61B 6/00* (2006.01)
*G06T 11/00* (2006.01)
(Continued)

(52) U.S. Cl.
CPC .......... *A61B 6/5235* (2013.01); *A61B 6/4435* (2013.01); *A61B 6/469* (2013.01);
(Continued)

(58) Field of Classification Search
CPC ....... A61B 6/5205; A61B 6/469; A61B 6/025; A61B 6/5235; G06T 11/003; G06T 11/008; G06T 2211/424
See application file for complete search history.

(56) References Cited

U.S. PATENT DOCUMENTS 6,480,565 B1 * 11/2002 Ning ...................... A61B 6/032
378/20
6,510,241 B1 * 1/2003 Vaillant .................. A61B 6/583
345/419
(Continued)

FOREIGN PATENT DOCUMENTS

FR 2680095 11/1993

*Primary Examiner* — David J Makiya
*Assistant Examiner* — Soorena Kefayati
(74) *Attorney, Agent, or Firm* — Boyle Fredrickson, S.C.

(57) ABSTRACT

A method of optimizing images of a patient utilizing a medical imaging device includes the steps of providing a medical imaging device having an x-ray source, an x-ray detector, a controller for adjusting the positions of the x-ray source and detector, an image reconstructor/generator connected to the x-ray detector to receive x-ray data and reconstruct an x-ray image, and a processor connected to the image reconstructor/generator and the controller to perform analyses on the x-ray image, acquiring a first data set $S_1$ of images, processing the first data set $S_1$ to reconstruct a first computerized data set $D_1$, analyzing the first computerized data set $D_1$, acquiring at least one additional data set $S_n$ in response to the analysis of the first computerized data set $D_1$ and processing the at least one additional data set $S_n$ in combination with the first data set $S_1$ to reconstruct an optimized computerized data set $D_n$.

11 Claims, 4 Drawing Sheets

(51) Int. Cl.
*A61B 6/02* (2006.01)
*A61B 6/03* (2006.01)
(52) U.S. Cl.
CPC ............ *A61B 6/502* (2013.01); *A61B 6/5205* (2013.01); *A61B 6/5247* (2013.01); *A61B 6/545* (2013.01); *G06T 11/006* (2013.01); *A61B 6/025* (2013.01); *A61B 6/032* (2013.01); *G06T 2211/424* (2013.01)

(56) References Cited

U.S. PATENT DOCUMENTS

| | | | |
|---|---|---|---|
| 6,714,621 B2 | 3/2004 | Rick et al. | |
| 6,848,826 B2 | 2/2005 | Marie et al. | |
| 7,564,937 B2* | 7/2009 | Nakanishi | A61B 6/032 378/4 |
| 7,693,254 B2 | 4/2010 | Muller et al. | |
| 7,912,176 B2* | 3/2011 | Bani-Hashemi | A61B 6/502 378/16 |
| 8,588,499 B2* | 11/2013 | Kubo | H01J 37/20 382/131 |
| 8,649,479 B2 | 2/2014 | DeMan et al. | |
| 8,977,027 B2* | 3/2015 | Da Silva | G06T 11/008 382/131 |
| 8,983,161 B2* | 3/2015 | Berkus | A61B 6/5205 378/164 |
| 8,995,734 B2* | 3/2015 | Papageorgiou | G06K 9/6206 382/131 |
| 9,042,510 B2* | 5/2015 | Voland | G01N 23/046 378/4 |
| 9,202,294 B2* | 12/2015 | Vija | G06F 19/321 |
| 9,271,691 B2* | 3/2016 | Dennerlein | A61B 6/032 |
| 10,064,593 B2* | 9/2018 | Ma | G06T 11/006 |
| 2006/0251308 A1* | 11/2006 | Grosskopf | A61B 5/107 382/128 |
| 2006/0269040 A1* | 11/2006 | Mertelmeier | A61B 6/466 378/37 |
| 2007/0009080 A1* | 1/2007 | Mistretta | G06T 11/006 378/4 |
| 2007/0083101 A1* | 4/2007 | Rietzel | A61B 6/032 600/407 |
| 2008/0167552 A1 | 7/2008 | Bouchevreau et al. | |
| 2008/0199063 A1* | 8/2008 | O'Halloran | G01R 33/4824 382/131 |
| 2008/0242968 A1* | 10/2008 | Claus | A61B 6/032 600/407 |
| 2011/0058724 A1* | 3/2011 | Claus | G06T 11/006 382/132 |
| 2011/0210261 A1* | 9/2011 | Maurer, Jr. | A61N 5/10 250/393 |
| 2012/0189102 A1* | 7/2012 | Maurer, Jr. | A61N 5/1081 378/65 |
| 2013/0211245 A1* | 8/2013 | Vembar | A61B 6/032 600/428 |
| 2013/0279783 A1* | 10/2013 | Schmitt | A61B 6/032 382/131 |
| 2013/0342577 A1* | 12/2013 | Wang | G06T 11/60 345/634 |
| 2014/0093030 A1* | 4/2014 | Mukumoto | A61B 8/12 378/4 |
| 2014/0286554 A1* | 9/2014 | Campagna | G06T 1/20 382/131 |
| 2014/0314203 A1* | 10/2014 | Helm | A61B 6/4476 378/62 |
| 2014/0328531 A1* | 11/2014 | Lee | G06T 19/00 382/131 |
| 2014/0376691 A1* | 12/2014 | Hoernig | G06T 11/006 378/37 |
| 2015/0086097 A1* | 3/2015 | Chen | G06T 11/008 382/131 |
| 2015/0238157 A1* | 8/2015 | Shi | A61B 6/5205 378/4 |
| 2015/0317820 A1* | 11/2015 | Choi | G06T 15/08 382/132 |
| 2016/0012636 A1* | 1/2016 | Lauritsch | G06T 11/60 345/420 |
| 2016/0278719 A1* | 9/2016 | Jensen | A61B 6/027 |
| 2016/0307339 A1* | 10/2016 | Miura | G06T 11/005 |
| 2017/0105695 A1* | 4/2017 | Ma | G06T 11/006 |

\* cited by examiner

ITERATIVE X-RAY IMAGING OPTIMIZATION METHOD AND SYSTEM

BACKGROUND OF INVENTION

Embodiments of the invention relate generally to X-ray medical imaging, and more particularly to systems and methods to perform standard digital mammography (DM), 2D/3D spectral mammography (SM) or digital breast tomosynthesis (DBT) guided biopsy exams, as well as in examinations of other types of tissues that can be imaged in these and other manners.

Spectral mammography (SM) is an x-ray two-dimensional (2D) imaging modality used to scan breasts for screening, diagnosis and/or interventional examination. The effectiveness of mammography is affected by numerous factors Alternative systems to SM are also known for breast imaging. For example, a digital breast tomosynthesis (DBT) or mammography-tomography (mammo-tomo) system is a dedicated mammography system that acquires several (e.g., tens of) projection images acquired at different locations and reconstructs three-dimensional (3D) image datasets.

In these procedures, a number of image acquisitions are performed, with each image taken at a different position of the X-ray source with respect to the detector. With regard to these procedures, current x-ray examinations for SM or DBT are populated with distinct datasets representing the images taken of the breast tissue from various angles in order to provide sufficient information about the tissue being imaged. These datasets include, for example, images taken of the cranio-caudal (CC) view and/or of the medial lateral oblique (MLO) view and/or of the medio-lateral (ML) or lateromedial (LM) views and views obtained by DBT, and combinations thereof, in a typical mammography examination.

Once these images are obtained, the images/datasets are then recombined to display material-specific information with regard to the internal structure of the tissue being imaged. Image recombination can be performed based on simulations of the X-ray image chain, which in one suitable exemplary manner is described in United States Patent Application Publication No. 2008/0167552, which is expressly incorporated by reference herein in its entirety, via calibrations on a reference phantom, or any other suitable 3D-reconstruction process, as is known.

Once the views or datasets taken in the procedure are recombined in the appropriate manner, an analysis of the recombined images is undertaken to locate any areas or regions of interest (ROI) in the recombined images.

With the images taken at the various angles to provide the standard views discussed above, it is often difficult to accurately correlate the data from the images in the different datasets with one another. Further, depending upon the results of this analysis, it is often necessary to re-acquire the images forming the individual datasets in order to refine the analysis of the ROI for diagnostic purposes. For, example, in French Patent No. 2,680,095, the analysis of the images in a first dataset is undertaken in order to adjust the set-up of the imaging device for taking a second set of images at a more optimal location for imaging the ROI. This re-acquisition is undesirable due to the length of time necessary for obtaining and analyzing the images, as well as the hazards associated with repeatedly dosing the tissue with radiation to produce the images for the datasets.

Accordingly, it is desirable to develop a medical imaging system and method to enhance the integration of datasets obtained from various images to focus on an ROI in the tissue being imaged. The medical imaging system should allow an existing image dataset to be updated or refined by combining the existing dataset with datasets from additional images as taken as determined from the analysis of the dataset(s) that have already been acquired and other contextual information, such as information related to the patient or the examination room, among others.

BRIEF DESCRIPTION OF THE INVENTION

There is a need or desire for a medical imaging system and method of obtaining images that enables an existing data set of images taken of a patient/tissue to be enhanced by combining the existing data set with additional images taken as a result of an analysis of the existing data set. The above-mentioned drawbacks and needs are addressed by the embodiments described herein in the following description.

According to one exemplary embodiment of the invention, a medical imaging system is provided that enables the user to interactively refine and optimize computerized image data during an imaging examination procedure. The system and method enables the user to acquire and add selected images to a first data set of images and other pre-existing data sets, instead of adding distinct image sets, which are difficult to correlate to one another. The additional image/data set acquisitions are taken and combined with the first and other existing data sets in order to provide added focus on or refinement/optimization of the areas/regions of interest that are located in the first and other pre-existing data sets in an initial analysis of those data sets. This optimization or refinement of the image data sets can be utilized for the enhancement of virtually any 2D or 3D image data set obtained from an imaging system, including the enhancement of the volume reconstruction of CT or DBT 3D images, for image recombination/linage decomposition in spectral imaging, and for providing super-resolution, i.e., to increase the image resolution on a given ROI in standard mammography.

According to one exemplary aspect of the invention, a medical imaging system, such as an x-ray computed tomography (CT) system or digital breast tomosynthesis (DBT) system is provided that includes a rotating gantry, an x-ray source coupled to the gantry for generating an x-ray beam and an x-ray detector coupled to the gantry for detecting x-rays of the x-ray beam. The x-ray CT or DBT system further includes an adjustable collimator coupled to the x-ray source and configured to adjust a focus of the x-ray beam generated by the x-ray source. The x-ray CT or DBT system also includes a controller configured to control the collimator to adjust the focus on a region of interest (ROI) and to control a beam intensity for the x-ray beam generated by the x-ray source during a scan. In operation, the controller operates the CT or DBT system to obtain a first dataset from a number of images taken of the tissue being investigated. This first dataset is then processed in the controller to reconstruct the volume of the tissue being investigate or any derivate representation of the first dataset. The reconstructed volume or 3D image is then analyzed to determine any region(s) of interest (ROI) in the reconstructed 3D volume. Based on the result of this analysis, the controller can operate the CT or DBT system to acquire an additional, e.g. second dataset on a selected portion or portions of the reconstructed volume. This second dataset is then combined with the first dataset to reconstruct the same volume or a portion of the same volume that is focused on the ROI, which is again analyzed with a focus on the ROI. The process can be repeated to achieve a reconstructed 3D volume of the ROI that provides the clinician with an optimized, highly accurate and high image quality (IQ) representation of the ROI.

According to another aspect of an exemplary embodiment of the invention, the medical imaging system enables the acquisition geometry to be optimized for the individual patient to achieve the highly accurate and enhanced image quality (IQ) representation of the ROI in either a 2D or 3D image.

According to another aspect of an exemplary embodiment of the invention, the medical imaging system can arrive at this highly accurate and optimized representation of the ROI without using completely distinct images or datasets, which are difficult to correlate with one another. Further, the avoidance of taking completely separate images consequently reduces the total radiation dosage received by the patient.

According to still a further aspect of one exemplary embodiment of the invention, a method of optimizing and/or enhancing images of tissue of a patient utilizing a medical imaging device includes the steps of providing a medical imaging device having an x-ray source for emitting x-rays, an x-ray detector for detecting the x-rays emitted from the x-ray source, a controller for adjusting the positions of the x-ray source and the x-ray detector relative to one another, an image reconstructor operably connected to the x-ray detector to receive x-ray data therefrom to reconstruct an x-ray image, and a processor operably connected to the image reconstructor and the controller and configured to perform analysis on the x-ray image, acquiring a first data set $S_1$ for a patient positioned on the medical imaging device, processing the first data set $S_1$ to reconstruct a first computerized data set $D_1$, analyzing the computerized data set $D_1$, acquiring at least one additional data set $S_n$ in response to the analysis of the computerized data set $D_1$ and processing the at least one additional data set $S_n$ in combination with the first data set $S_1$ to reconstruct an updated computerized data set $D_n$.

According to still another aspect of one exemplary embodiment of the invention, a method for optimizing medical images of a patient includes the steps of providing a medical imaging device having an x-ray source for emitting x-rays, an x-ray detector for detecting the x-rays emitted from the x-ray source, a support on which a subject or organ to be imaged is positioned, a controller for adjusting the positions of the x-ray source and the x-ray detector relative to one another, an image generator operably connected to the x-ray detector to receive x-ray data therefrom to generate processed data and a processor operably connected to the image generator and the controller and configured to perform analysis on the x-ray image, acquiring a (where n is ≥1) image data sets $S_1$ to $S_n$ for a patient of organ positioned on the support, processing a subset of the image data sets $S_1$ to $S_n$ including at least one of image data sets $S_1$ to $S_n$ to generate a first processed data set $D_n$, analyzing the first processed data set $D_n$, defining the acquisition parameters for an additional input data set $S_{n+1}$, acquiring at least one additional image data set $S_{n+1}$ and processing the at least additional image data set $S_{n+1}$ to obtain an additional processed data $D_{n+1}$.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION OF THE DRAWINGS

Figure 1:
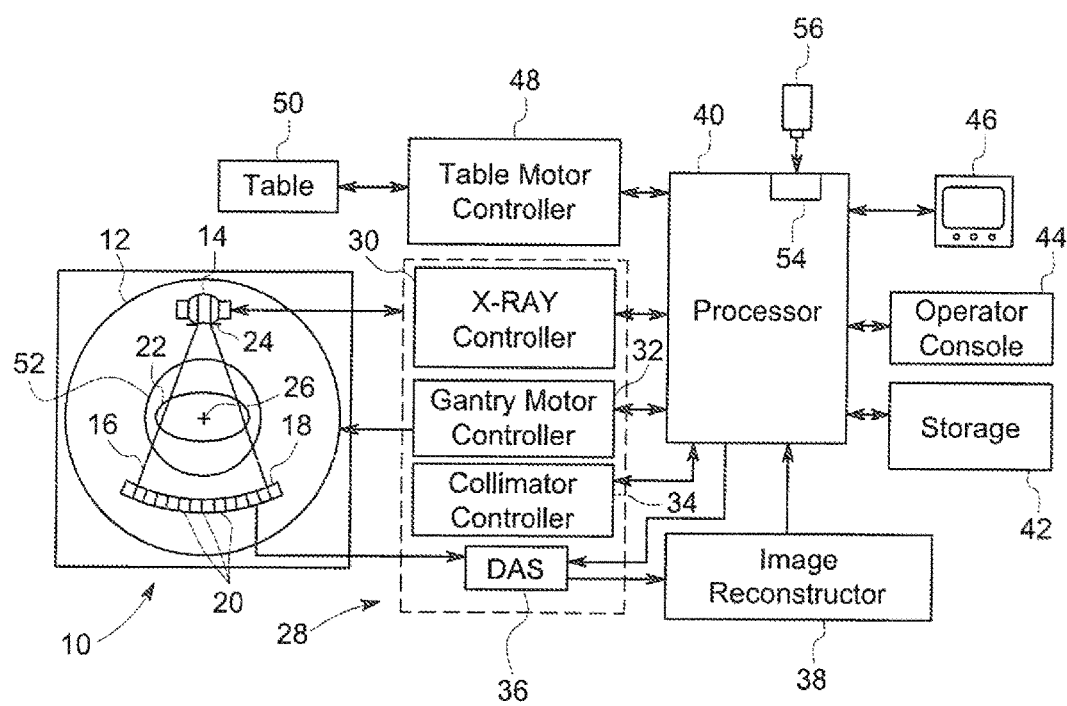
FIG. 1 is a block diagram illustrating an x-ray computed tomography (CT) imaging system formed according to one exemplary embodiment of the present invention.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Further, the foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

Various embodiments provide a system and method for obtaining 2D or 3D images of selected tissue in a patient, including but not limited to x-ray computed tomography (CT) or digital breast tomosynthesis (DBT) breast imaging. The CT or DBT breast imaging is performed in any suitable manner, such as by using dynamic region of interest (ROI) collimation control with varying x-ray beam intensity. At least one technical effect of the various embodiments is the ability to perform breast imaging using an imaging system that is not configured for dedicated breast imaging. For example, by practicing at least some embodiments, breast imaging may be performed using a CT or DBT architecture with a patient imaged in a supine position.

FIG. 1 illustrates a simplified block diagram of an x-ray imaging system 10 operable to perform breast imaging in accordance with one exemplary embodiment of the invention, such as that disclosed in co-owned U.S. Pat. No.

8,649,479, the entirety of which is expressly incorporated by reference herein. However, other alternative systems can be utilized in place of the system 10, including a SenoBright® or SenoClaire® device manufactured by GE Healthcare, or other CT or DBT systems and/or devices similar to those disclosed in U.S. Pat. Nos. 6,714,621; 6,848,826 and 7,693,254, each of which is expressly incorporated herein by reference in its entirety.

The x-ray system 10 may be configured as a multi-slice scanning imaging system that includes a gantry 12, which may be representative of a third generation imaging system as described in more detail herein. The gantry 12 generally includes (e.g., supports thereon) an x-ray source 14 (also referred to as an x-ray tube) that projects an x-ray beam 16 towards a detector array 18 on the opposite side of the gantry 12. The detector array 18 is formed by a plurality of detector rows (not shown) including a plurality of detector elements 20 that together sense the projected x-rays that pass through an object, such as a patient 22 (e.g., a female patient having breast scanning performed) positioned in a supine (or optionally prone or standing) position between the detector array 18 and the x-ray source 14.

A collimator 24 is provided in combination with the x-ray source 14 to collimate and focus the x-ray beam 16. In various embodiments, the intensity level and the collimation of the generated x-ray beam 16 are dynamically controlled and adjusted. For example, as described in more detail herein, dynamic breast ROI collimation and sensitive organ power modulation are provided in accordance with various embodiments.

With respect to the detector array 18, each detector element 20 produces an electrical signal that represents the intensity of an impinging x-ray beam and hence can be used to estimate the attenuation of the beam as the beam passes through the patient 22. During a scan to acquire x-ray projection data, the gantry 12 and the components mounted therein rotate about a center of rotation 26. It should be noted that although only a single row of detector elements 20 (i.e., a detector row) is shown, the detector array 18 in various embodiments is a multi-slice detector array having a plurality of parallel detector rows of detector elements 20, such that projection data corresponding to a plurality of quasi-parallel or parallel slices can be acquired simultaneously during a scan.

Rotation of the components on the gantry 12 and operation of the x-ray source 14 and collimator 24 are governed by a control mechanism 28 of the CT system 10. The control mechanism 28 includes an x-ray controller 30 that provides power and timing signals to the x-ray source 14, a gantry motor controller 32 that controls the rotational speed and position of components on the gantry 12, and a collimator controller 34 that controls collimation of the x-ray source 14 to adjust and define an ROI, For example, a field of view (FOV) of the collimator 24 is adjusted using dynamic collimation.

A data acquisition system (DAS) 36 in the control mechanism 28 samples analog data from the detector elements 20 and converts the data to digital signals for subsequent processing. An image reconstructor/generator 38 receives sampled and digitized x-ray data from the DAS 36 and performs image reconstruction. The reconstructed image is communicated to a processor 40 (e.g., a computer), which stores the image in a storage device 42. The image reconstructor/generator 38 can be specialized hardware or computer programs executing on the processor 40, for example, as a module.

The processor 40 also receives commands and scanning parameters from an operator via an operator console 44 that includes input devices, such as a keyboard, mouse, etc. An associated display 46 is provided, which may be any suitable display type that allows the operator to view the reconstructed image(s) and other data from the processor 40. The operator supplied commands and parameters may be used by the processor 40 to provide control signals and information to the DAS 36, x-ray controller 30, gantry motor controller 32 and collimator controller 34 as described in more detail herein. In addition, the processor 40 operates a table motor controller 48, which controls a motorized patient table 50 to position the patient 22 in the gantry 12. Particularly, the table 50 moves portions of the patient 22 through a gantry opening 52. It should be noted that the patient 22 (or a portion of the patient 22) may be moved into the gantry 12 and during imaging remain stationary during rotation of the gantry 12 or may move the patient 22 through the opening 52 during as the gantry 12 rotates.

In various embodiments, the processor 40 includes a device 54, for example, a CD-ROM drive, a DVD drive, a magnetic optical disk (MOD) device, a USB port, or any other digital device including a network connecting device such as an Ethernet device for reading instructions and/or data from a computer-readable medium 56, such as a floppy disk, a CD-ROM, a DVD, a flash memory drive (illustrated in FIG. 1) or another digital source such as a network or the Internet, as well as yet to be developed digital means. In other embodiments, the processor 40 executes instructions stored in firmware (not shown). The processor 40 is programmed to perform functions described herein, and as used herein, the term processor is not limited to just those integrated circuits referred to in the art as computers, but broadly refers to computers, microcontrollers, microcomputers, programmable logic controllers, application specific integrated circuits, and other programmable circuits, and these terms are used interchangeably herein.

Although the above-described embodiment refers to a third generation imaging system, the methods described herein equally apply to fourth generation imaging systems (stationary detector-rotating x-ray source) and fifth generation imaging systems (stationary detector and x-ray source). Additionally, it is contemplated that the benefits of the various embodiments accrue to other imaging modalities. Further, although the herein described methods and apparatus are described in a particular medical setting, it is also contemplated that the benefits of the various embodiments accrue to other applications or settings.

In operation, referring now to FIGS. 2-4, in one exemplary embodiment of the invention, the imaging system 10 is operated in the following steps:
1. acquire a first data set $S_1$;
2. process the first data set $S_1$ using the processor to obtain a first processed or computerized data set $D_1$;
3. analyze the data contained in the first computerized data set $D_1$;
4. based on the analysis result of the first computerized data set $D_1$, plan and perform an acquisition of an additional data set $S_n$; and
5. return to step 2 to process the additional data set $S_n$ with the first data set $S_1$ as well as any other additional data sets $\{S_{n-1}, S_{n-2}, \ldots, S_1\}$ and/or the first computerized data set $D_1$ and any additional computerized data sets $\{D_{n-1}, D_{n-2}, \ldots, D_1\}$ to reconstruct an updated computerized data set $D_n$, from $S_n$ in combination with the additional data sets $\{S_{n-1}, S_{n-2}, \ldots, S_1\}$ and/or the additional computerized data sets $\{D_{n-1}, D_{n-2}, \ldots, D_1\}$.

In another exemplary embodiment of the invention, the imaging system 10 including a support, e.g., gantry 12, is operated in the following steps:

1. acquire a first data set $S_1$;
2. acquiring n (where n is ≥1) data sets $S_1$ to $S_n$, for a patient or organ positioned on the support;
3. processing a subset of the data sets $S_1$ to $S_n$ including at least one of $S_1$ to $S_n$ to generate a first processed data set $D_n$;
4. analyzing the first processed data set $D_n$;
5. defining the acquisition parameters for an additional input data set $S_{n+1}$
6. acquiring at least one additional data set $S_{n+1}$
7. processing the at least additional input data set $S_{n+1}$ to obtain an additional processed data $D_{n+1}$.

Figure 2:
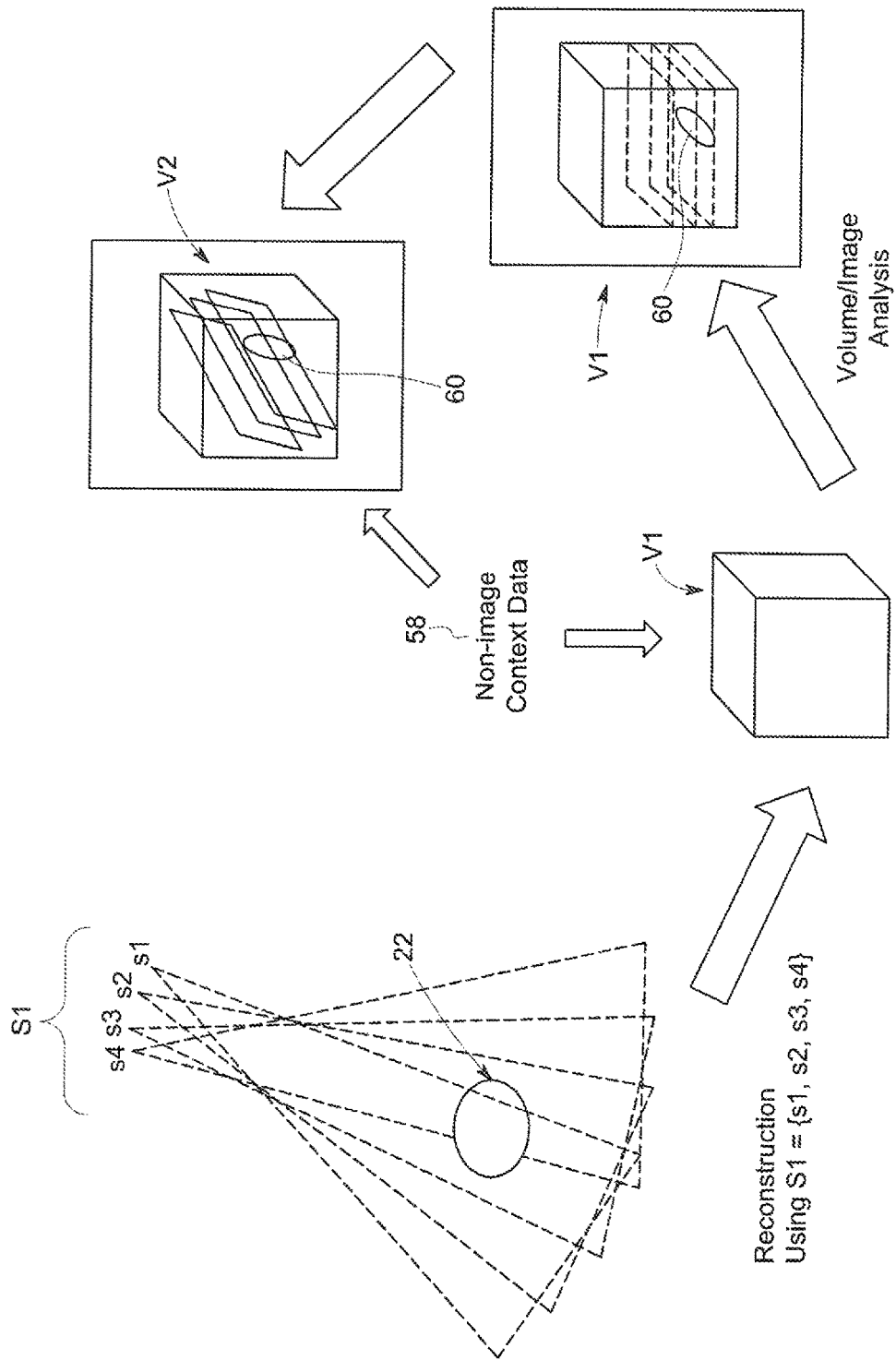
FIG. 2 is a schematic representation of a first acquisition step according to an exemplary embodiment of the invention.
Figure 3:
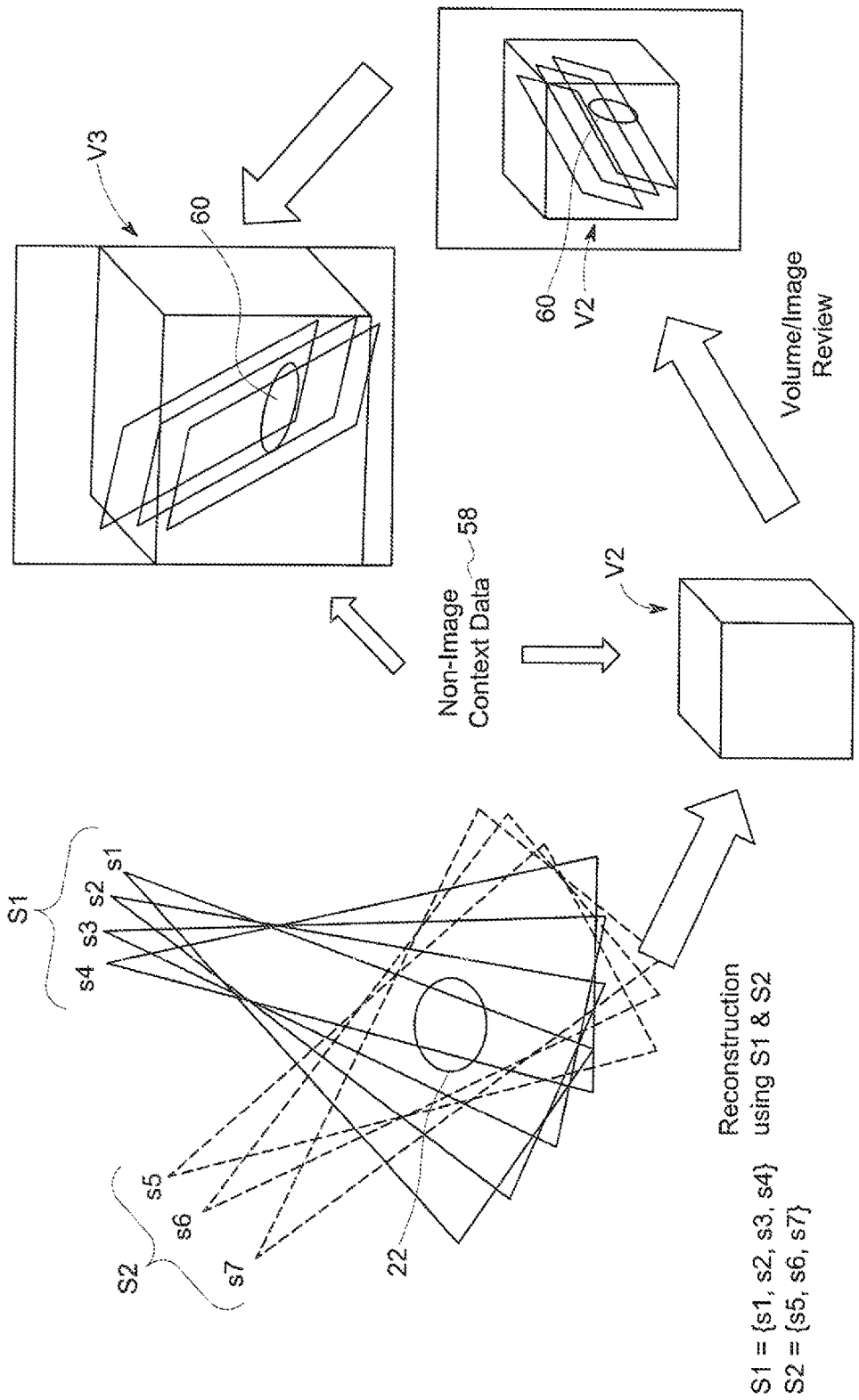
FIG. 3 is a schematic representation of a second acquisition step according to an exemplary embodiment of the invention.

In particular, looking at the exemplary embodiment illustrated in FIG. 2, in step (1) the system 10, which in the illustrated embodiment is a 3D CT imaging system, is operated to obtain the first data set $S_1$ including images s1, s2, s3 and s4. These images s1-s4 are then transmitted to the image reconstructor 38 which performs image reconstruction to create the first computerized data set $D_1$ and optionally a corresponding 2D image according to step (2). In 3D imaging systems 10, a 3D first volume $V_1$ is formed from the first computerized data set $D_1$ using the images s1-s4 from the first data set $S_1$ in conjunction with other non-image contextual data 58 obtained by the system 10. The non-image contextual data 58 can include, but is not limited to, information relating to the particular patient 22 or the exam room, for example.

Once completed, the reconstructed image or first volume $V_1$ is communicated to a processor 40 (e.g., a computer), for analysis is step (3). The analysis performed in step (3) can be performed by the user, by the computer 40 such as by using pattern recognition/image analysis algorithms or CAD-like engines, as are known in the art. The analysis can also be performed jointly by the user and the computer 40, such as where the computer 40 analyzes the first computerized data set $D_1$ and corresponding 2D image or first volume $V_1$, presents regions of interest (ROI) 60 in the tissue 22, such as in a breast region, lung region or other sensitive organ region of the patient 22 to the user, and the user selects the particular ROIs 60 for further investigation.

Once selected, using the first computerized data set $D_1$ and corresponding 2D image or the first volume $V_1$ and other information, such as, but not limited to the non-image contextual information 58, the processor/computer 40 can determine the desired and/or alternative angles and/or orientations for additional images s5, s6 and s7 (FIG. 3) to be taken of the ROIs 60 in step (4) that will provide a better and enhanced image of the selected ROIs 60 for diagnostic purposes.

When the desired orientations for the additional images s5-s7 to be taken have been determined in step (4), the system 10 again operates according to step (2) to position the x-ray source 14 relative to the detector 18 in order to obtain the additional images s5-s7 of the tissue 22, which form a second (or first additional) data set 58. The data sets $S_1$ and $S_2$ are then combined and analyzed and/or utilized by the image reconstructor/generator 38 in step (2) to create a second computerized data set $D_2$ and/or a second volume $V_2$, again in conjunction with any relevant non-contextual information 58. The second computerized data set $D_2$ and corresponding 2D image or second volume $V_2$ corresponds to the desired orientation for the 2D or 3D image determined from the analysis of the first computerized data set $D_1$ and corresponding 2D image first volume $V_1$ in order to provide the user with an enhanced image of the ROIs 60 selected within the first computerized data set $D_1$ and corresponding 2D image or first volume $V_1$.

After the second computerized data set $D_2$ and corresponding 2D image or second (or first updated) volume $V_2$ is reconstructed using the data sets $S_1$ and $S_2$, the second computerized data set $D_2$ and/or second volume $V_2$ is analyzed similarly to the first computerized data set $D_1$ and corresponding 2D image or first volume $V_1$ in step (3) to provide further information about the ROIs 60 and any additional or desired orientation for the 2D or 3D image, as well as the orientation of any additional image(s) s8 that are required to achieve this orientation.

Figure 4:
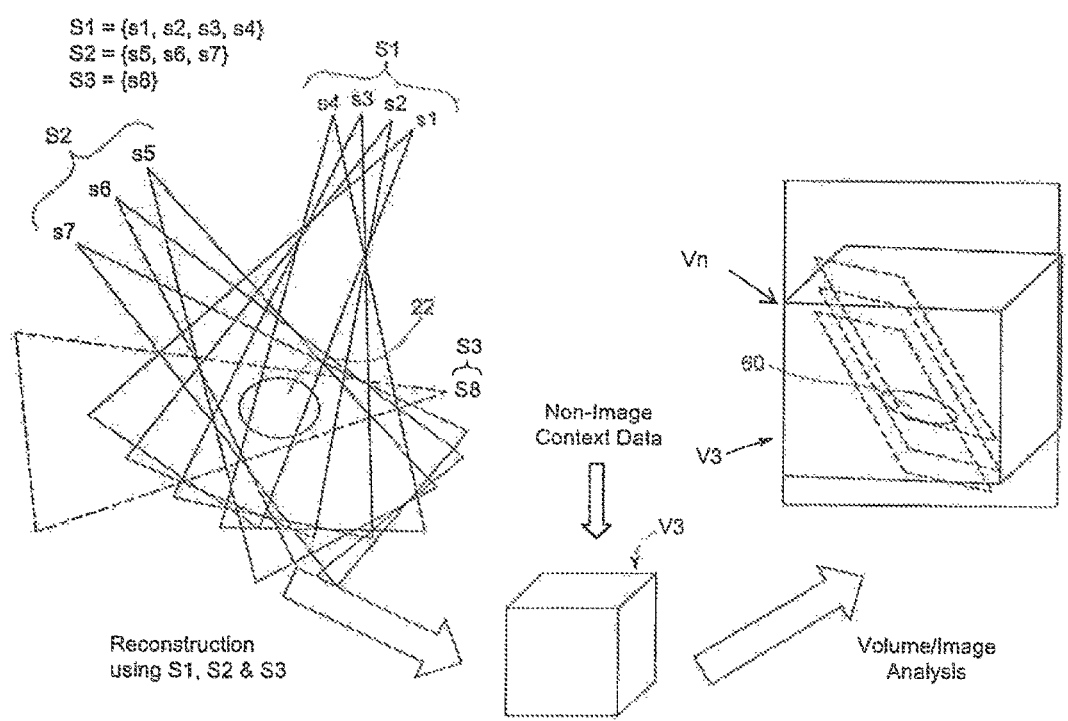
FIG. 4 is a schematic representation of a third acquisition step according to an exemplary embodiment of the invention.

With this information, the system 10 can again be operated according to step 4 to position the source 14 and detector 18 to obtain the desired additional image(s) s8, thereby forming a third data set $S_3$, as shown in FIG. 4. This third (or second additional) data Set $S_3$ is combined with data sets $S_1$ and $S_2$, as well as non-image contextual data 58, for processing by image reconstructor/generator 38 for forming the third computerized data set $D_3$ and corresponding 2D image or third (or second updated) volume $V_3$ in step (2). Once formed, the third computerized data set $D_3$ and corresponding 2D image or third volume $V_3$ is analyzed in step (3) to provide optimized and high quality image information regarding the selected ROIs 60 contained within the third computerized data set $D_3$ and corresponding 2D image or third volume $V_3$.

In certain alternative exemplary embodiments for 3D images, the data sets $S_1, S_2, \ldots S_n$ can be combined with one another and optionally with the pre-existing volumes $V_1, V_2, \ldots V_{n-1}$ to arrive at the corresponding updated computerized data set $D_n$ enhanced volume $V_n$. In an alternative exemplary embodiment for 3D images, the enhanced volume $V_n$ can be formed only be combining the pre-existing volumes $V_1, V_2, \ldots V_{n-1}$ after each volume $V_1, V_2, \ldots V_{n-1}$ has been reconstructed from the combined data sets $S_1, S_2, \ldots S_n$.

Regardless of how the enhanced computerized data set $D_n$ and/or volume $V_n$ is determined, in the illustrated exemplary method of the invention the acquisition geometry required for obtaining the images s1, s2, . . . etc., used to form the data sets $S_1$, $S_2$, $S_3$, etc., can be relaxed compared to standard mammography/DBT systems as a result of the ability of successive data set acquisitions to enhance the image quality (IQ) of the resulting computerized data set $D_n$ and/or volume $V_n$ when combined to reconstruct the computerized data set $D_n$ and/or volume $V_n$. For example, when using the method of the invention in a 3D imaging system, the source 14 and/or detector 18 do not need to be restricted in terms of their position(s) in the 3D space relative to the patient 22, thereby enabling more degrees of freedom with regard to the acquisition of the images s1-s8, for example. Further, in mammography procedures, the compression of the tissue 22 can be relaxed as a result of the enhancement of the computerized data set $D_n$ and/or volume $V_n$ by combining each successive data set $S_1$, $S_2$, $S_3$, etc., to form the computerized data set $D_n$ and/or volume $V_n$, thereby making the procedure painless (e.g., prone table or robotic gantry). Further, in the case where the system 10 includes a robotic gantry 12, the detector 18 and gantry 12 can move in synchronization with one another or when the detector 18 is not secured to the patient this configuration is useful to implement zoom/superesolution with regard to the images in the computerized data set(s) $D_n$.

Also, in certain exemplary embodiments of the invention the additional acquisitions of data sets are characterized by the time the data set is obtained during the procedure, the particular positions of the x-ray source 14 and/or detector 18, and/or the overall configuration of the system 10, such as KV, mas, filter, collimation blades, etc., can be triggered directly by the user's analysis or request, or may result from an automated analysis of previously acquired data sets $S_1$, $S_2$, etc. and any other additional of information, including, but not limited to the non-image contextual information 58.

Further, without regard to the particular manner in which the need for additional data set acquisitions are determined, the additional acquisitions done during the overall acquisition with the same settings for the system 10 are always coherent with already acquired data sets $S_1$, $S_2$, etc. As a result, the pre-existing computerized data, such as the computerized data sets $D_1, D_2, \ldots D_n$, which can take the form of reconstructed volumes $V_1, V_2, \ldots V_{n-1}$, recombined images (decomposition on a material basis), a combination of 2D images (e.g., to provide enhanced resolution, reduced-noise, image compositions) or 2D re-projections, slabs, etc., are always enhanced and/or refined by additional views or images s(n) forming the data sets from the additional acquisitions. In other words, the image optimization or enhancement works for any processed computerized image data including: volume reconstruction in CT/DBT, recombination/image decomposition in spectral imaging, and super-resolution to significantly increase the image resolution on a given ROI in standard mammography.

In addition, as a result of the iterative analysis of the method on the computerized data sets $D_1, D_2, \ldots D_n$ and/or the reconstructed volumes $V_1, V_2, \ldots, V_n\_1$, the geometry of the additional acquisitions or views can be adapted according to the organ content allowing focusing on suspicious areas/ROIs 60 located in the analyses, with the potential to allocate doses of x-ray only on these selected areas/ROIs 60. The interaction between the processor 40 conducting the analysis and the geometry of the system 10 to be used for the acquisition of the successive images s(n) can assist the user of the system 10 in defining the parameters of the images s(n) to be acquired. For example, in systems 10 displaying 3D images, the system 10 can provide an overlay on a display of the current volume $V_{n-1}$ that shows where the IQ of one or more ROIs 60 within the current volume $V_{n-1}$ or image penetration of some tissues (e.g. an implant) will be improved when a new image(s) s(n) is taken with the system 10 in the current position. In the case of a co-manipulated robot (not shown) enabling the motion of at least one component 14, 18, etc., of the imaging system 10, some virtual guides (not shown) can be implemented, such as on the display 46, to assist the operator to manually move via the console 44 the component 14, 18, etc., to the initial position for the next data set acquisition. Additional views can be used to refine findings in some orientations to magnify some areas or even to better penetrate some tissues within the patient 22, such as an implant.

Using the system 10 and the associated method, it is possible to optimize the geometry for the acquisition of the additional data sets $S_2, S_3, \ldots, S_n$ for each corresponding enhanced or updates computerized data set(s) $D_n$ or volume(s) $V_n$ for the patient who is imaged. This is because the focal spot positions used during all the successive acquisitions are selected according to the analysis of the initial and/or pre-existing computerized data set(s) $D_1$, $D_2, \ldots D_{n-1}$ or volume(s) $V_1, V_2, \ldots, V_{n-1}$ as reconstructed from the first or pre-acquired data sets $S_1$, $S_2$, etc., and the resulting determination of what ROIs 60 need to be enhanced in the updated or enhanced computerized data set $D_n$ and/or volume $V_n$.

In conjunction with the analysis by the system 10 or as a separate feature of the system 10, the user can select one or more ROIs 60 in the analyzed computerized data set(s) $D_1$, $D_2, \ldots D_{n-1}$ or volume $V_1, V_2, \ldots,$ or $V_{n-1}$ to locally maximize the image quality in a successive acquisition step, such as to provide localized magnification on a particular POI 60 in the analyzed computerized data set(s) $D_1$, $D_2, \ldots D_{n-1}$ or volume $V_1, V_2, \ldots,$ or $V_{n-1}$. In one exemplary embodiment, in a standard mammography exam, a magnified image s(n), such as an image taken with the source 14 closer to the patient 22 and centered on an ROI 60, can be selected and acquired for addition and/or combination with the pre-existing data set $S_1$ corresponding to a standard imaging or mammography procedure. Because the first data set $S_1$ and magnified image s(n) are processed/reconstructed together, the resulting updated or enhanced computerized data set $D_n$ or volume $V_n$ has a higher resolution on the ROI 60, allowing the user to zoom in on the selected ROI 60, for example, a calcification cluster. Further, this modification to the method for use of the system 10 can be successively applied to multiple ROIs 60 that are combined with the initial or pre-existing data set $S_1$, such that the enhanced volume $V_n$ has a higher resolution on each of the ROIs 60 present in the enhanced volume $V_n$.

As an additional benefit of the system 10 and method, because the additional acquisitions or data sets $S_2, S_3, \ldots$, $S_n$ are normally select images that entail less than a full array of images normally obtained in a standard imaging or mammography procedure, the radiation dose received by the patient 22 can be lessened significantly. For example, if the first acquisition/data set $S_1$ is obtained at a very low radiation dose, and only a sub-section of the imaged tissue in the patient 22, e.g., the breast, is selected for the additional acquisitions or data sets $S_2, S_3, \ldots, S_n$, those portions of the tissue not selected for further imaging will be exposed to a much lower level of radiation as compared to the situation where a standard full dose imaging procedure is utilized for each subsequent acquisition or data sets $S_2, S_3, \ldots, S_n$.

Further, because the first acquisition/data set $S_1$ is continually updated with the additional data sets $S_2, S_3, \ldots, S_n$ that are acquired, in an exemplary embodiment of the method of the invention, the system 10 and method of the invention provides an easier workflow, especially in biopsy examinations/procedures, as there is no need to correlate distinct views of the tissue being imaged.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Further, the ordering of the dependent claims is also considered to be exemplary, such that it is also within the scope of the invention that each dependent claim be considered to be combinable with every other claim to form various alternative embodiments of the invention.

What is claimed is:

1. A method for optimizing medical images of a patient comprising the steps of;

providing a medical imaging device having an x-ray source for emitting x-rays, an x-ray detector for detecting the x-rays emitted from the x-ray source, a controller for adjusting the positions of the x-ray source and the x-ray detector relative to one another, an image generator operably connected to the x-ray detector to receive x-ray data therefrom to generate processed data, and a processor operably connected to the image generator and the controller and configured to perform analysis on an x-ray image;

acquiring a first data set $S_1$;

processing the first data set $S_1$ using the processor to obtain a first processed or computerized data set $D_1$ and first volume $V_1$;

analyzing data contained in the first computerized data set $D_1$;

performing an acquisition of at least one additional data set $S_2, S_3, \ldots,$ or $S_n$ based on an analysis result of the first computerized data set $D_1$ and first volume $V_1$, wherein n (where n is ≥1) image data sets $S_1$ to $S_n$ each include a different number of images;

processing the first data set $S_1$ in combination with the at least one additional data set $S_2, S_3, \ldots,$ or $S_n$ using the processor to obtain a second processed or computerized data set $D_2$ and second volume $V_2$; and combining the first volume $V_1$ and the second volume $V_2$ to form an enhanced volume $V_n$.

2. The method of claim 1, wherein the step of acquiring at least one additional data set $S_2, S_3, \ldots,$ or $S_n$ comprises:

acquiring a first additional data set $S_2$;

processing the first additional data set $S_2$ in combination with the first data set $S_1$ to reconstruct a second computerized data set $D_2$;

analyzing the second computerized data set $D_2$;

acquiring a second additional data set $S_3$; and processing the second additional data set $S_3$ in combination with the first data set $S_1$ and the first additional data set $S_2$ to reconstruct a third computerized data set $D_3$.

3. The method of claim 1, wherein the at least one additional data set $S_2, S_3, \ldots,$ or $S_n$ has a number of images less than that of the first data set $S_1$.

4. The method of claim 2 further comprising processing the first additional data set $S_2$ in combination with the first data set $S_1$ and non-image contextual data to reconstruct the second computerized data set $D_2$.

5. The method of claim 2, wherein the step of analyzing the first computerized data set $D_1$ comprises:

determining an image quality of at least one ROI identified in the first computerized data set $D_1$; and determining an optimal orientation for acquiring the first additional data set $S_2$ including the at least one ROI.

6. The method of claim 2, wherein the step of analyzing the first computerized data set $D_1$ comprises identifying a number of ROIs in the first computerized data set $D_1$.

7. The method of claim 2, wherein the first additional data set $S_2$ has a number of images less than the first data set $S_1$.

8. The method of claim 5, wherein the step of analyzing the second computerized data set $D_2$ comprises:

determining an image quality enhancement of the at least one ROI in the second computerized data set $D_2$; and determining an optimal orientation for acquiring the second additional data set $S_3$ including the at least one ROI.

9. The method of claim 6, wherein the step of acquiring the first additional data set $S_2$ comprises acquiring at least one image of each of the ROIs for inclusion in the first additional data set $S_2$.

10. The method of claim 9, wherein the step of acquiring at least one image of each of the ROIs comprises acquiring at least one magnified image of each of the ROIs.

11. The method of claim 7, wherein the second additional data set $S_3$ has a number of images less than the first additional data set $S_2$.

* * * * *